United States Patent [19]

Krämer et al.

[11] 4,151,287
[45] Apr. 24, 1979

[54] COMBATING FUNGI WITH 1-DIARYLOXY-1-TRIAZOLYL-3,3-DIMETHYL-BUTAN-2-ONES AND BUTAN-2-OLS

[75] Inventors: Wolfgang Krämer; Karl Heinz Buchel, both of Wuppertal; Wilhelm Brandes, Cologne; Helmut Kaspers, Leverkusen, all of Fed. Rep. of Germany

[73] Assignee: Bayer Aktiengesellschaft, Leverkusen, Fed. Rep. of Germany

[21] Appl. No.: 779,861

[22] Filed: Mar. 21, 1977

Related U.S. Application Data

[63] Continuation of Ser. No. 629,428, Nov. 6, 1975, abandoned.

[30] Foreign Application Priority Data

Nov. 27, 1974 [DE] Fed. Rep. of Germany ....... 2455955

[51] Int. Cl.² ............... A01N 9/00; C07D 249/08
[52] U.S. Cl. ............... 424/269; 260/308 R; 260/308 A
[58] Field of Search ............ 424/269; 260/308 A, 260/308 R

[56] References Cited

U.S. PATENT DOCUMENTS 3,912,752  10/1975  Meiser et al. ............... 260/308 R
4,002,763  1/1977   Meiser et al. ............... 424/269

Primary Examiner—Leonard Schenkman
Attorney, Agent, or Firm—Sprung, Felfe, Horn, Lynch & Kramer

[57] ABSTRACT

Compositions containing, and methods of combating fungi using, 1-diaryloxy-1-triazolyl-3,3-dimethyl-butan-2-ones and -butan-2-ols of the formula

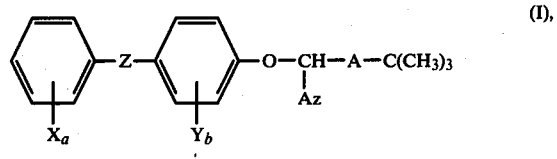

(I), in which
X and Y each independently is halogen, nitro, alkyl, alkoxy, halogenoalkylthio, amino, alkylamino, dialkylamino or N-alkyl-alkylsulfonylamino,
Z is a direct bond, oxygen, sulfur, methylene, alkoxymethylene, sulfonyl or keto,
A is —CO— or —CH(OH)—,
Az is 1,2,4-triazolyl-(1), 1,2,4-triazolyl-(4) or 1,2,3-triazolyl-(1), and
a and b each independently is 0, 1, 2 or 3,
or salts thereof. Some of the compounds are new.

10 Claims, No Drawings

COMBATING FUNGI WITH 1-DIARYLOXY-1-TRIAZOLYL-3,3-DIMETHYL-BUTAN-2-ONES AND BUTAN-2-OLS

This is a continuation of application Ser. No. 629,428, filed Nov. 6, 1975, now abandoned.

The present invention relates to and has for its objects the provision of particular fungicidal compositions containing, and methods of combating fungi using, 1-diaryloxy-1-triazolyl-3,3-dimethyl-butan-2-ones and -butan-2-ols or salts thereof. The compositions are in the form of mixtures of such compounds with solid and liquid dispersible carrier vehicles. Other and further objects will become apparent from a study of the within specification and accompanying examples.

It has been disclosed in German Published Specification DOS 2,201,063 that triazolyl-O,N-acetals, such as, for example, 1-(p-chlorophenoxy)-1-[1,2,4-triazolyl-(1)]-3,3-dimethylbutan-2-one (Compound A), in general possess a very good fungicidal activity. However, their action is not always entirely satisfactory in certain indication categories, especially if low amounts and low concentrations are used.

It has been found that the diaryloxy-triazolyl-O,N-acetals of the general formula $$\text{(I)}$$

[Structure: phenyl ring with $X_a$ substituent — Z — phenyl ring with $Y_b$ substituent — O—CH(Az)—A—C(CH$_3$)$_3$]

in which
X and Y each independently is halogen, nitro or an alkyl, alkoxy, halogenoalkylthio, amino, alkylamino, dialkylamino or N-alkylalkylsulfonylamino group,
Z is a direct bond, oxygen, sulfur, methylene, alkoxymethylene, sulfonyl or keto,
A is —CO— or —CH(OH)—,
Az is a 1,2,4-triazolyl-(1), 1,2,4-triazolyl-(4) or 1,2,3-triazolyl-(1) radical, and
a and b each independently is 0, 1, 2 or 3,
and their salts exhibit powerful fungicidal properties.

Surprisingly, the active compounds according to the invention, and their salts, exhibit a substantially greater fungicidal action than the triazolyl-O,N-acetals known from the state of the art, such as 1-(p-chlorophenoxy)-1-[1,2,4-triazolyl-(1)]-3,3-dimethylbutan-2-one, which are the nearest active compounds of the same type of action. A particularly good action is achieved against phytopathogenic fungi of the genus Erysiphe. The active compounds according to the invention thus represent an enrichment of the art.

Preferably, X and Y are each fluorine, chlorine, bromine, alkyl with up to 4 carbon atoms (for example methyl, ethyl, isopropyl and tertiary butyl), alkoxy with up to 4 (especially with up to 2) carbon atoms (such as methoxy), halogenoalkylthio with up to 4 carbon atoms and up to 5 halogen atoms (especially with up to 2 carbon atoms and up to 3 identical or different halogen atoms selected preferably from fluorine and chlorine, of which substituents the trifluoromethylthio group may be mentioned as an example), nitro, amino or an alkylamino, dialkylamino or N-alkyl-alkylsulfonylamino group with up to 4 (especially with up to 2) carbon atoms in each alkyl group (of which the ethylamino, dimethylamino and N-methyl-methylsulfonylamino groups may be mentioned as examples); a and b are each 0, 1 or 2; and Z is a direct bond, oxygen, sulfur, a methylene, sulfonyl or carbonyl group or a methoxy-methylene or ethoxy-methylene group.

Some compounds of the formula (I) have been prepared and described in German Patent Application P 24 01 715.0 filed January 15, 1974. However, a sub-genus not specifically disclosed in that application and having an interesting fungicidal action comprises those compounds of the formula (I).
in which
X, Y, Z, A, Az and b have the meanings stated above and
a is 1, 2 or 3 and may also be 0, provided Z does not denote a direct bond or oxygen.

Those compounds of the formula (I) in which A is a keto (carbonyl) group are obtained when (a) the correspondingly substituted 1-aryloxy-1-halogeno-3,3-dimethylbutan-2-ones are reacted, in a manner which is known in principle, with triazoles, if appropriate in the presence of an acid-binding agent and if appropriate in the presence of a diluent, preferably in the temperature range between 60° and 120° C.

Those compounds of the formula (I), in which the bridge member A is a hydroxymethylene group, can be obtained in a manner which is known in principle by (b) reducing the keto compounds obtained according to (a), either 1. with hydrogen in the presence of a catalyst and if appropriate in the presence of polar solvents, preferably in the temperature range between 20° and 40° C., or 2. with aluminum isopropanolate in the presence of a solvent, preferably at between 50° and 100° C., or 3. with a complex hydride, if appropriate in the presence of a polar solvent, preferably at from 0° to 20° C., or 4. with formamidinesulfinic acid and alkali metal hydroxide, if appropriate in the presence of a polar solvent, preferably at between 50° and 100° C.

More detailed information thereon is to be found in the preparative Examples hereinbelow.

The reduced compounds of the formula (I) have two asymmetrical carbon atoms; they can therefore be in the erythro-form and in the threo-form. In both cases they are predominantly present as racemates.

The following may be mentioned as suitable appropriately substituted 1-aryloxy-1-halogeno-3,3-dimethyl-butan-2-ones which can be converted, by reaction (a) with triazoles, into compounds of the formula (I) which can be used according to the invention: 1-bromo-1-[4'-(3"-methylphenyl)-phenoxy]-3,3-dimethylbutan-2-one, 1-bromo-1-[4'-(2"-chlorophenyl)-(3'-chlorophenoxy)]-3,3-dimethylbutan-2-one, 1-bromo-1-[4'-(2"-bromo-4"-chlorophenyl)-(2'-bromophenoxy)]-3,3-dimethylbutan-2-one, 1-chloro-1-[4'-(4"-nitrophenyl)-(2',6'-dichlorophenoxy)]-3,3-dimethylbutan-2-one, 1-chloro-1-[4'-(4"-ethoxyphenyl)-(2'-bromo-6'-chlorophenoxy)]-3,3-dimethylbutan-2-one, 1-chloro-1-[4'-(3"-aminophenyl)-(2'-methylphenyl)-]-3,3-dimethylbutan-2-one, 1-chloro-1-[4'-(2"-methylphenoxy)-(2'-chlorophenoxy)]-3,3-dimethylbutan-2-one, 1-chloro-1-[4'-(3"-chlorophenoxy)-phenoxy]-3,3-dimethylbutan-2-one, 1-chloro-1-[4'-phenoxy-2',6'-dibromophenoxy]-3,3-dimethylbutan-2-one, 1-bromo-1-[4'-(3"-nitrophenylthio)-(2'-bromophenoxy)]-3,3-dimethylbutan-2-one, 1-bromo-1-[4'-(2"-methoxyphenylthio)-(2'-chlorophenoxy)]-3,3-dimethylbutan-2-one, 1-bromo-1-[4'-(4"-bromophenylthio)-(3'- chlorophenoxy)]-3,3-dimethylbutan-2-one, 1-bromo-1-[4'-(2''-chlorophenylsulfonyl)-phenoxy]-3,3-dimethylbutan-2-one, 1-bromo-1-[4'-(4''-ethylphenylsulfonyl)-(2',6'-dichlorophenoxy)]-3,3-dimethylbutan-2-one, 1-chloro-1-[4'-(2''-chlorophenylcarbonyl)-(2'-bromophenoxy)]-3,3-dimethylbutan-2-one, 1-chloro-1-[4'-(2'',6''-dichlorophenylcarbonyl)-(2'-chlorophenoxy)]-3,3-dimethylbutan-2-one, 1-chloro-1-[4'-(2''-nitrophenylcarbonyl)-phenoxy]-3,3-dimethylbutan-2-one, 1-chloro-1-[4'-(4''-bromobenzyl)-(3'-bromophenoxy)]-3,3-dimethylbutan-2-one, 1-chloro-1-[4'-(4'''-trifluoromethylthiobenzyl)-(2',3'-dichlorophenoxy)]-3,3-dimethylbutan-2-one, 1-chloro-1-[4'-(3'',5''-dichlorobenzyl)-(2'-methylphenoxy)]-3,3-dimethylbutan-2-one, 1-bromo-1-[4'-(4''-tert.-butylbenzyl)-phenoxy]-3,3-dimethylbutan-2-one and 1-bromo-1-[4'-(2''-ethylaminobenzyl)-(2'-nitrophenoxy)]-3,3-dimethylbutan-2-one.

The aryloxy-1-halogeno-3,3-dimethylbutan-2-ones required as intermediates have not previously been described in the literature. They can be prepared according to a process which has long been known (the so-called "Williamson ether synthesis"), by reacting the corresponding phenol components with a 1-halogeno-3,3-dimethylbutan-2-one in the presence of a hydrogen halide acceptor and, in a subsequent reaction, replacing the residual active hydrogen atom in the 1-position by halogen in the usual manner.

Possible salts of the compounds of the formula (I) are salts with physiologically tolerated acids, especially the hydrogen halide acids, such as hydrochloric acid and hydrobromic acid, phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and finally sulfonic acids, such as 1,5-naphthalenedisulfonic acid.

The salts of the compounds of the formula (I) can be obtained in a simple manner in accordance with customary methods of forming salts, for example by dissolving the base in an ether, for example diethyl ether, and adding the acid, for example hydrogen chloride, and can be isolated in a known manner, for example by filtering off, and be purified if appropriate.

The active compounds to be used according to the invention exhibit a powerful fungitoxic action. They do not damage crop plants in the concentrations required for combating fungi. For this reason, they are suitable for use as plant protection agents for combating fungi. Fungitoxic agents are employed in plant protection for combating Archimycetes, Phycomycetes, Ascomycetes, Basidiomycetes and *Fungi Imperfecti.*

The active compounds according to the invention have a broad spectrum of action and can be employed against parasitic fungi which attack above-ground parts of plants or attack the plants through the soil, and against seed-borne pathogens. They display a particularly good activity against parasitic fungi on above-ground parts of plants, such as species of Erysiphe, species of Podosphaeara and species of Venturia, for example against the pathogen of powdery mildew of apples (*Podosphaera leucotricha* and the pathogen of apple scab (*Fusicladium dendriticum*). Furthermore, they display a high activity against diseases of cereals, such as powdery mildew of cereals and cereal rust.

As plant protection agents, the active compounds according to the invention can be used for the treatment of seed and for the treatment of above-ground parts of plants.

The compounds according to the invention are well tolerated by plants. They have only a low toxicity to warm-blooded animals and because of their low odor and their good toleration by human skin they are not unpleasant to handle.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene,alkyl naphthalenes, etc), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or insecticides, acaricides, nematocides, bactericides, rodenticides, herbicides, fertilizers, growth-regulating agents, bird repellents, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.00001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the prupose in question and which is generally between about 0.00001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used as leaf fungicides, for example, the active compound concentrations in the use forms can be varied within a fairly wide range. They are in general between 0.1 and 0.00001 percent by weight, preferably between 0.05 and 0.00001 percent.

In the treatment of seed, amounts of active compound of 0.001 to 50 g, especially 0.01 to 10 g, are generally required per kilogram of seed.

At somewhat higher concentrations, the compounds also exhibit growth-regulating properties.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular compounds of the present invention are illustrated, without limitation, by the following examples:

EXAMPLE 1

Mycelium growth test

Nutrient medium used:
  20 parts by weight of agar-agar
  200 parts by weight of potato decoction
  5 parts by weight of malt
  15 parts by weight of dextrose
  5 parts by weight of peptone
  2 parts by weight of disodium hydrogen phosphate
  0.3 part by weight of calcium nitrate
Ratio of solvent mixture to nutrient medium:
  2 parts by weight of solvent mixture
  100 parts by weight of agar nutrient medium

| Composition of the solvent mixture |
| --- |
| 0.19 part by weight of acetone |
| 0.01 part by weight of emulsifier (alkylaryl polyglycol ether) |
| 1.80 parts by weight of water |
| 2    parts by weight of solvent mixture |

The amount of active compound required for the desired active compound concentration in the nutrient medium was mixed with the stated amount of solvent. The concentrate was thoroughly mixed, in the stated proportion, with the liquid nutrient medium which had been cooled to 42° C. and was then poured into Petri dishes of 9 cm diameter. Control plates to which the preparation had not been added were also set up.

When the nutrient medium had cooled and solidified, the plates were inoculated with the species of fungi stated in the table and incubated at about 21° C.

Evaluation was carried out after 4–10 days, depending upon the speed of growth of the fungi. When evaluation was carried out the radial growth of the mycelium on the treated nutrient media was compared with the growth on the control nutrient medium. In the evaluation of the fungus growth, the following characteristic values were used:
  1 no fungus growth
  up to 3 very strong inhibition of growth
  up to 5 medium inhibition of growth
  up to 7 slight inhibition of growth
  9 growth equal to that of untreated control.

The active compounds, the active compound concentrations and the results can be seen from the following table:

Table 1

Mycelium growth test at an active-compound concentration of 10 ppm

| Active compound | Fungi | | | | | | | | | | | | | |
|---|---|---|---|---|---|---|---|---|---|---|---|---|---|---|
| | Fusarium culmorum | Sclerotinia sclerotiorum | Fusarium nivale | Colletotrichum coffeanum | Rhizoctonia soleni | Pythium ultimum | Cochliobolus miyaoceanus | Botrytis cinerea | Verticillium alboatrum | Pyricularia oryzae | Phialophora cinerescens | Helminthiosporium gramineum | Mycosphaerella musicola | Phytophthora cactorum | Pellicularia sasakii |
| (known) (A) [structure: 4-Cl-C6H4-O-CH(N-triazole)-CO-C(CH3)3] | 9 | 9 | 9 | 9 | 5 | 9 | 9 | 9 | 5 | 9 | 9 | 9 | 5 | 9 | 5 |
| (12) [structure: 2-Cl-4-(4-Cl-C6H4)-C6H3-O-CH(N-triazole)-CO-C(CH3)3] | — | — | — | — | — | — | — | — | — | — | — | 3 | 2 | 1 | 2 |
| (17) [structure: 2-Cl-4-(4-Cl-C6H4)-C6H3-O-CH(N-triazole)-CH(OH)-C(CH3)3] | — | 5 | — | 5 | 3 | 5 | 5 | 3 | — | 1 | 1 | 1 | 2 | 1 | — |
| (22) [structure: 4-C6H5-C6H4-O-CH(N-triazole)-CO-C(CH3)3] | 5 | 5 | 3 | 1 | .5 | 3 | 5 | — | 3 | — | — | 5 | 1 | 5 | 3 |
| (15e) [structure: 4-C6H5-C6H4-O-CH(N-triazole)-CH(OH)-C(CH3)3 × HCl] | 2 | — | 3 | 3 | 5 | 3 | 1 | 5 | 3 | 1 | 1 | 1 | 1 | 5 | 1 |
| (15d) [structure: 4-C6H5-C6H4-O-CH(N-triazole)-CH(OH)-C(CH3)3 × HNO3] | 3 | — | 3 | 3 | 5 | 3 | 1 | — | 3 | 3 | 3 | 1 | 1 | 3 | 1 |

Table 1-continued

Mycelium growth test at an active-compound concentration of 10 ppm

| Active compound | Fusarium culmorum | Sclerotinia sclerotiorum | Fusarium nivale | Colletotrichum coffeanum | Rhizoctonia soleni | Pythium ultimum | Cochliobolus miyaoeanus | Botrytis cinerea | Verticillium alboatrum | Pyricularia oryzae | Phialophora cinerescens | Helminthiosporium gramineum | Mycoephaerella musicala | Phytophthoea cactorum | Pellicularia sasakii |
|---|---|---|---|---|---|---|---|---|---|---|---|---|---|---|---|
| (15c) biphenyl-O-CH-CH-C(CH₃)₃ with OH, triazolyl, × ½ naphthalene-1,5-(SO₃H)₂ | 3 | 1 | 3 | 1 | 5 | 3 | 1 | 5 | 3 | 1 | 2 | 1 | 1 | 1 | 1 |
| (15b) biphenyl-O-CH-CH-C(CH₃)₃ with OH, triazolyl, × CH₃SO₃H | 3 | 1 | 5 | 5 | 1 | 5 | 1 | 5 | 5 | 1 | 5 | 1 | 1 | 1 | 1 |
| (15a) biphenyl-O-CH-CH-C(CH₃)₃ with OH, triazolyl, × H₂SO₄ | 3 | 1 | 3 | 3 | 1 | 5 | 1 | 5 | 3 | 1 | 5 | 1 | 1 | 1 | 1 |
| (14a) biphenyl-O-CH-CO-C(CH₃)₃ with triazolyl, × 3 H₃PO₄ | 1 | 1 | 1 | 5 | 5 | 5 | 5 | 1 | 1 | 5 | 1 | 2 | 1 | 1 | 5 |

EXAMPLE 2

Shoot treatment test/powdery mildew of cereals/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier and then 975 parts by weight of water were added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis var. hordei.*

After 6 days' dwell time of the plants at a temperature of 21°-22° C. and 80-90% atmospheric humidity the occurrence of mildew pustules on the plants was evaluated. The degree of infection was expressed as a percentage of the infection of the untreated control plants. 0% denotes no infection and 100% denotes the same degree of infection as in the case of the untreated control. The more active the compound, the lower is the degree of mildew infection.

The active compounds, active compound concentration in the spray liquor and degrees of infection can be seen from the table which follows:

Table 2

Shoot treatment test/powdery mildew of cereals/protective

| Active compounds | | Active compound concentration in the spray liquor, in % by weight | Infection in % of the untreated control |
|---|---|---|---|
| Untreated | | — | 100 |
| [2,6-dichlorophenoxy-CH(triazolyl)-CO-C(CH₃)₃] (known) | (B) | 0.01 | 91.3 |
| | | 0.001 | 91.3 |
| [2-biphenylyloxy-CH(triazolyl)-CO-C(CH₃)₃] (known) | (C) | 0.01 | 55.0 |
| | | 0.001 | 100 |
| [2,4-dichlorophenoxy-CH(triazolyl)-CO-CH₃ × HCl] (known) | (D) | 0.01 | 33.8 |
| | | 0.001 | 66.3 |
| [pentachlorophenoxy-CH(triazolyl)-CO-C(CH₃)₃ × H₂O] (known) | (E) | 0.01 | 60.0 |
| | | 0.005 | 90.0 |
| | | 0.001 | 100 |
| [2,4-dimethylphenoxy-CH(triazolyl)-CO-C(CH₃)₃] (known) | (F) | 0.01 | 82.5 |
| | | 0.001 | 100 |
| [4-phenoxyphenoxy-CH(triazolyl)-CO-C(CH₃)₃] | (5) | 0.01 | 3.8 |

Table 2-continued

Shoot treatment test/powdery mildew of cereals/protective

| Active compounds | | Active compound concentration in the spray liquor, in % by weight | Infection in % of the untreated control |
|---|---|---|---|
| Cl—⟨⟩—⟨⟩—O—CH—CO—C(CH₃)₃ with triazole | (1) | 0.01<br>0.001 | 21.3<br>27.5 |
| Cl—⟨⟩—⟨⟩—O—CH—CH—C(CH₃)₃ with triazole, OH | (2) | 0.01<br>0.001<br>0.0001 | 18.8<br>18.8<br>25.00 |
| ⟨⟩—CH₂—⟨⟩—O—CH—CO—C(CH₃)₃ with triazole | (7) | 0.01 | 0.0 |
| Cl—⟨⟩—⟨⟩(Cl)—O—CH—CO—C(CH₃)₃ with triazole | (12) | 0.01 | 15.0 |
| Cl—⟨⟩—⟨⟩(Cl)—O—CH—CH—C(CH₃)₃ with triazole, OH | | 0.01 | 3.8 |
| ⟨⟩—CH(OCH₃)—⟨⟩—O—CH—CH—C(CH₃)₃ with triazole, OH | (18) | 0.01<br>0.001 | 0.0<br>0.0 |
| ⟨⟩—⟨⟩—O—CH—CH—C(CH₃)₃ with triazole, OH × HNO₅ | (15d) | 0.01<br>0.001 | 0.0<br>0.0 |
| ⟨⟩—⟨⟩—O—CH—CH—C(CH₃)₃ with triazole, OH × ½ naphthalene-1,5-disulfonic acid | (17) | 0.01<br>0.001 | 0.0<br>0.0 |
| ⟨⟩—⟨⟩—O—CH—CH—C(CH₃)₃ with triazole, OH × CH₃SO₅H | (15b) | 0.01<br>0.001 | 0.0<br>0.0 |

Table 2-continued

Shoot treatment test/powdery mildew of cereals/protective

| Active compounds | | Active compound concentration in the spray liquor, in % by weight | Infection in % of the untreated control |
|---|---|---|---|
| [Biphenyl-O-CH(N-triazole)-CH(OH)-C(CH$_3$)$_3$ × H$_2$SO$_4$] | (15a) | 0.01 | 0.0 |
| | | 0.001 | 0.0 |

EXAMPLE 3

Shoot treatment test/cereal rust/protective
(leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension has dried on, the wheat plants were sprayed with the preparation of active compound until dew-moist and were placed, for incubation, in a greenhouse for 24 hours at about 20° C. and 100% relative atmospheric humidity.

After 10 days' dwell time of the plants at a temperature of 20° C. and 80–90% atmospheric humidity, the occurrence of rust pustules on the plants was evaluated. The degree of infection was expressed as a percentage of the infection of the untreated control plants. 0% denotes no infection and 100% denotes the same degree of infection as in the case of the untreated control. The more active the compound, the lower is the degree of rust infection.

The active compounds, active compound concentrations in the spray liquor and degrees of infection can be seen from the table which follows:

Table 3

Shoot treatment test/cereal rust/protective

| Active compounds | | Active compound concentration in the spray liquor in % by weight | Infection in % of the untreated control |
|---|---|---|---|
| Untreated | | — | 100 |
| [Phenyl-O-CH(N-triazole)-CO-phenyl] (known) | (G) | 0.025 | 90.0 |
| | | 0.01 | 90.0 |
| [2,4-dichlorophenyl-O-CH(N-triazole)-CO-4-chlorophenyl] (known) | (H) | 0.025 | 100 |
| | | 0.01 | 100 |
| [2,4-dichlorophenyl-O-C(phenyl)(N-triazole)-CO-C(CH$_3$)$_3$ × HCl] (known) | (A) | 0.025 | 82.5 |
| | | 0.01 | 100 |
| [4-chlorophenyl-O-CH(N-triazole)-CO-CH$_3$ × HCl] (known) | (J) | 0.025 | 86.3 |
| | | 0.01 | 86.3 |

Table 3-continued

Shoot treatment test/cereal rust/protective

| Active compounds | | Active compound concentration in the spray liquor in % by weight | Infection in % of the untreated control |
|---|---|---|---|
| 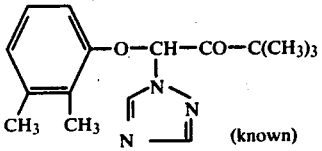 (known) | (K) | 0.025<br>0.01 | 88.8<br>100 |
| 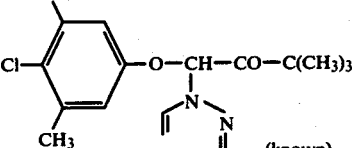 (known) | (L) | 0.025<br>0.01 | 75.0<br>75.0 |
| 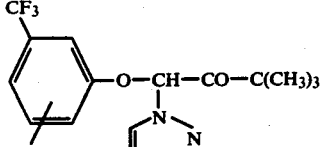 (known) | (M) | 0.025<br>0.01 | 90.0<br>90.0 |
| 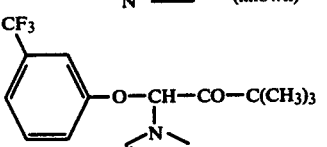 (known) | (N) | 0.025<br>0.01 | 100<br>100 |
| 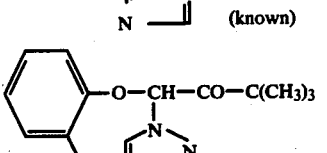 (known) | (O) | 0.025<br>0.01 | 70.0<br>85.0 |
| 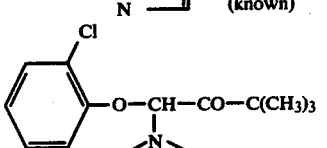 (known) | (P) | 0.025<br>0.01 | 100<br>90.0 |
| 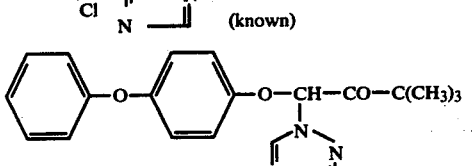 | (5) | 0.025 | 21.3 |
| 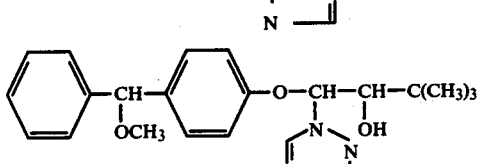 | (18) | 0.025<br>0.01 | 25.0<br>50.0 |

EXAMPLE 4

Erysiphe test

Solvent: 4.7 parts by weight of acetone

Emulsifier: 0.3 part bY weight of alkylaryl polyglycol ether

Water: 95 parts by weight

The amount of the active compound required for the desired concentration of active compound in the spray liquid was mixed with the stated amount of the solvent, and the concentrate was diluted with the stated amount of water containing the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoracearum*. The plants were subsequently placed in a greenhouse at 23°–24° C. and at a relative atmospheric humidity of about 75%.

After 12 days, the infection of the cucumber plants was determined as a percentage of the untreated but also inoculated control plants. 0% means no infection; 100% means that the infection was exactly as great as in the case of the control plants.

The active compounds, the concentrations of the active compounds and the results can be seen from the following table:

vent, and the concentrate was diluted with the stated amount of water which contained the stated additions.

Young apple seedlings in the 4–6 leaf stage were sprayed with the spray liquid until dripping wet. The plants remained in a greenhouse for 24 hours at 20° C. and at a relative atmospheric humidity of 70%. They were then inoculated by dusting with conidia of the apple powdery mildew causative organism (*Podosphaera leucotricha*) and placed in a greenhouse at a temperature of 21°–23° C. and at a relative atmospheric humid- Table 4

Erysiphe test

| Active compound | Infection in % of the infection of the untreated control at an active compound concentration (in %) of | |
|---|---|---|
| | 0.00019 | 0.000125 |
| 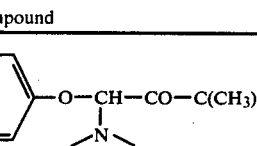 (A) (known) | 19 | — |
| 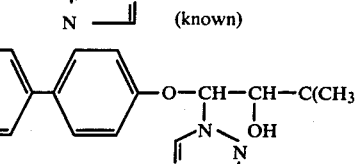 (2) | — | 6 |
| 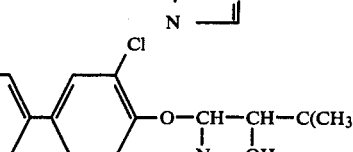 (17) | — | 12 |

EXAMPLE 5

Podophaera test (powdery mildew of apples)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solity of about 70%.

Ten days after the inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from the following table:

Table 5

Podosphaera test/protective

| Active compound | Infection in % of the infection of the untreated control at an active compound concentration of | |
|---|---|---|
| | 0.00078% | 0.00062% |
| 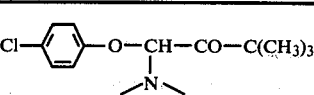 (known) (A) | 26 | — |
| 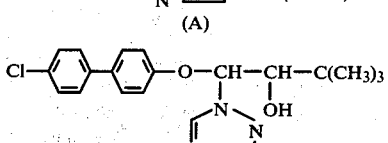 (2) | — | 24 |

EXAMPLE 6

Uromvces test (bean rust)/protective

Solvent: 4.7 parts by weight of acetone
Emulsifier: 0.3 part by weight of alkylaryl polyglycol ether
Water: 95 parts by weight The amount of active compound required for the desired concentration of active compound in the spray liquor was mixed with the stated amount of the solvent and the concentrate was diluted with the stated amount of water which contained the stated additives.

The young bean plants, which were in the 2-leaved stage, were sprayed with the spray liquor until dripping wet. The plants remained in a greenhouse for 24 hours at 20°-22° C. and a relative atmospheric humidity of 70% in order to dry. They were then inoculated with an aqueous uredospore suspension of the causative organism of bean rust (*Uromvces phaseoli*) and incubated for 24 hours in a dark humidity chamber at 20°-22° C. and 100% relative atmospheric humidity.

The plants were then set up in a greenhouse under intensive illumination for 9 days at 20°-22° C. and a relative atmospheric humidity of 70-80%.

10 days after the inoculation, the infection of the plants was determined in % of the untreated but also inoculated control plants.

0% denotes no infection and 100% denotes that the infection was just as high as in the case of the control plants.

The active compounds, active compound concentrations and results can be seen from the table which follows:

Table 6

| Uranvose test/protective | |
|---|---|
| Active compound | Infection in % of the infection of the untreated control at an active compound concentration of 0.00156% |
| 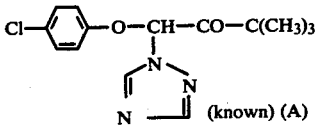 (known) (A) | 91 |
| 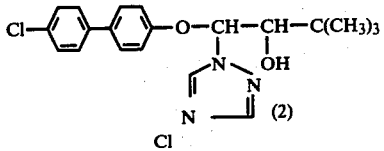 (2) | 50 |
| 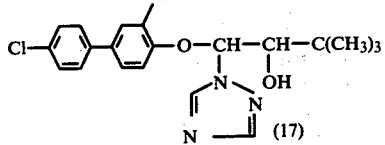 (17) | 35 |
| 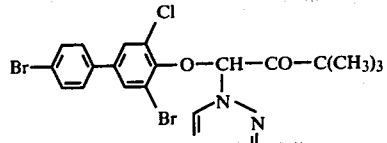 (11) | 82 |

Table 6-continued

| Uranvose test/protective | |
|---|---|
| Active compound | Infection in % of the infection of the untreated control at an active compound concentration of 0.00156% |
| 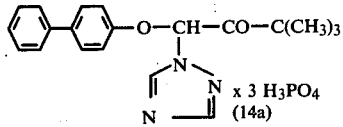 (14a) | 0 |

EXAMPLE 7

(a) Preparation of the intermediate:

204.5 g (1 mole) of 4-(4'-chlorophenyl)-phenol (prepared by halogenation of p-phenyl-phenoxy-acetate followed by hydrolysis) were dissolved in 1 liter of methyl ethyl ketone and 140 g (1 mole) of potassium hydroxide were added. The mixture was heated to the reflux temperature and 134.5 g (1 mole) of 1-chloropinacolone were then slowly added dropwise. The reaction mixture was kept under reflux for 6 hours and was then freed from the solid residue. After distilling off the solvent, the mixture was recrystallized from 600 ml of ligroin. 240 g (79% of theory) of 1-(4''-chlorophenyl)-phenoxy)-3,3-dimethylbutan-2-one of melting point 90° C. were obtained.

60.5 g (0.2 mole) of this compound were dissolved in carbon tetrachloride. 10.2 ml (0.2 mole) of bromine were added dropwise at room temperature at a rate such that steady consumption occurred. After distilling off the solvent in vacuo, crude 1-bromo-1-[4'-(4''-chlorophenyl)-phenoxy]-3,3-dimethylbutan-2-one was obtained.

b) 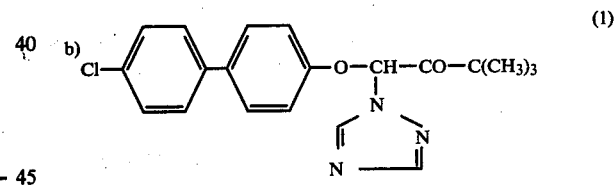 (1)

76.2 g (0.2 mole) of crude 1-bromo-1-[4'-(4''-chlorophenyl)-phenoxy]-3,3-dimethylbutan-2-one were dissolved in 500 ml of acetonitrile. 48 g (0.6 mole) of 1,2,4-triazole were added and the mixture was heated for 48 hours under reflux. It was then concentrated by distilling off the solvent. 200 ml of water were added to the residue and the mixture was extracted by shaking with three times 100 ml of methylene chloride. The organic phases were combined, dried over sodium sulfate and concentrated in a water-pump vacuum. 100 ml of ligroin were added to the residue and the mixture was heated under reflux, with addition of 50 ml of ethyl acetate. The solid which remained thereafter was filtered off hot. 8.6 g (11% of theory) of 1-[4'-(4''-chlorophenyl)-phenoxy]-1-[1,2,4-triazolyl-(4)]-3,3-dimethylbutan-2-one of melting point 210°-212° C. were obtained as a by-product. The filtrate was concentrated in a water-pump vacuum by distilling off the solvent. The residue was recrystallized from ligroin. 52.8 g (72% of theory) of 1-[4'-(4''-chlorophenyl)-phenoxy]-1-[1,2,4-triazolyl-(1)]-3,3-dimethylbutan-2-one of melting point 116°-118° C. were obtained.

EXAMPLE 8

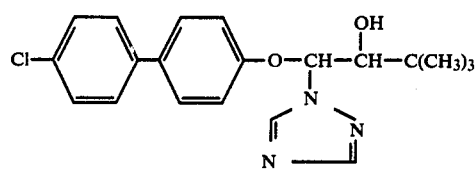

(Preparation according to process (b))

2.5 g (0.075 mole) of sodium borohydride were added to 18.5 g (0.05 mole) of 1-[4'-(4''-chlorophenyl)-phenoxy]-1-[1,2,4-triazolyl-(1)]-3,3-dimethylbutan-2-one, dissolved in 200 ml of methanol, at 5° to 10° C. The reaction mixture was stirred for 1 hour at room temperature. After acidifying with 20 ml of concentrated hydrochloric acid, the reaction mixture was left to stand for 15 hours and was then stirred into 500 ml of saturated sodium bicarbonate solution. The mixture was then extracted by shaking with three times 100 ml of methylene chloride. The solvent was distilled off from the combined organic phases in a water-pump vacuum and 100 ml of petroleum ether were added to the residue. The crystals which had precipitated were filtered off. 16.8 g (90% of theory) of white crystals of 1-[4'-(4''-chlorophenyl)-phenoxy]-1-[1,2,4-triazolyl-(1)]-3,3-dimethylbutan-2-ol (erythro-form and threo-form) of melting point 135°–146° C. were obtained.

The following compounds of the general formula

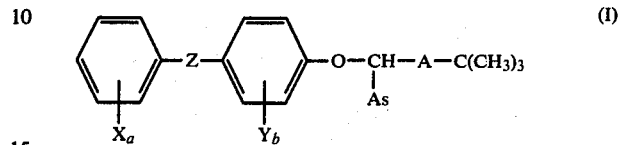

were obtained analogously:

Table 7

| Compound No. | X | a | Y | b | Z | Az | A | Melting point (° C.) |
|---|---|---|---|---|---|---|---|---|
| 3 | — | 0 | 2-Cl | 1 | — | 1,2,4-Triazolyl-(1) | CO | 107 |
| 4 | — | 0 | 2,6-Cl$_2$ | 2 | — | " | CO | 149–150 |
| 5 | — | 0 | — | 0 | —O— | " | CO | 98 |
| 6 | — | 0 | — | 0 | —SO$_2$— | " | CO | 150 |
| 7 | — | 0 | — | 0 | —CH$_2$— | " | CO | 95–99 |
| 8 | 4-Br | 1 | 2,6-Cl$_2$ | 2 | — | " | CO | 150–152 |
| 9 | 4-NCH$_3$<br>\|<br>SO$_2$CH$_3$ | 1 | — | 0 | — | " | CO | 171–173 |
| 10 | 4-OCH$_3$ | 1 | — | 0 | — | " | CO | 108–109 |
| 11 | 4-Br | 1 | 2-Br, 6-Cl | 2 | — | " | CO | 148–150 |
| 12 | 4-Cl | 1 | 2-Cl | 1 | — | " | CO | 101–102 |
| 13 | — | 0 | — | 0 | —CO— | " | CO | 125–126 |
| 14a | — | 0 | — | 0 | — | " | CO | 124–126 (x 3H$_3$PO$_4$) |
| 15a | — | 0 | — | 0 | — | " | CHOH | 135–140 (x H$_2$SO$_4$) |
| 15b | — | 0 | — | 0 | — | " | CHOH | 132–34 (x CH$_3$SO$_3$H) |
| 15c | — | 0 | — | 0 | — | " | CHOH | 170–177 (x ½ 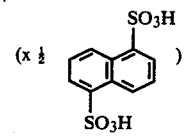) |
| 15d | — | 0 | — | 0 | — | 1,2,4-Triazolyl-(1) | CHOH | 152–165 (x HNO$_3$) |
| 15e | — | 0 | — | 0 | — | " | CHOH | 75–82 (x HCl) |
| 16 | — | 0 | — | 0 | —CH$_2$— | " | CHOH | 93–106 |
| 17 | 4-Cl | 1 | 2-Cl | 1 | — | " | CHOH | 88–95 |
| 18 | — | 0 | — | 0 | —CH—<br>\|<br>OCH$_3$ | " | CHOH | 103–109 |
| 19 | 4-Br | 1 | 2-Br, 6-Cl | 2 | — | 1,2,4-Triazolyl-(4) | CO | 186–188 |
| 20 | 4-Cl | 1 | — | 0 | — | " | CO | 210–212 |
| 21 | — | 0 | — | 0 | —SO$_2$— | " | CHOH | 198–202 |
| 22 | — | 0 | — | 0 | — | 1,2,3-Triazolyl-(1) | CO | 107–108 |

Other compounds which can be similarly prepared include:

Table 8

| Compound No. | X | a | Y | b | Z | Az | A |
|---|---|---|---|---|---|---|---|
| 23 | 4-NO$_2$ | 1 | 2,6-Cl$_2$ | 2 | — | 1,2,4-Triazolyl-(1) | CO |
| 24 | 4-OC$_2$H$_5$ | 1 | 2-Br,6-Cl | 2 | — | 1,2,4-Triazolyl-(1) | CO |
| 25 | 3-NO$_2$ | 1 | 2-Br | 1 | —S— | 1,2,4-Triazolyl-(1) | CO |
| 26 | 2,6-Cl$_2$ | 2 | 2-Cl | 1 | —CO— | 1,2,4-Triazolyl-(1) | CO |
| 27 | 2-NO$_2$ | 1 | — | 0 | —CO— | 1,2,4-Triazolyl-(1) | CO |
| 28 | 4-SCF$_3$ | 1 | 2,3-Cl$_2$ | 2 | —CH$_2$— | 1,2,4-Triazolyl-(1) | CO |
| 29 | 4-C$_4$H$_9$tert. | 1 | — | 0 | —CH$_2$— | 1,2,4-Triazolyl-(1) | CO |
| 30 | 2-NHC$_2$H$_5$ | 1 | 2-NO$_2$ | 1 | —CH$_2$— | 1,2,4-Triazolyl-(1) | CO |
| 31 | 4-SCCl$_2$F | 1 | 2,6-F$_2$ | 2 | — | 1,2,4-Triazolyl-(1) | CO |
| 32 | 4-N(CH$_3$)$_2$ | 1 | 2-NH$_2$ | 1 | — | 1,2,4-Triazolyl-(1) | CO |
| 33 | 4-C$_3$H$_7$i | 1 | 2-OC$_3$H$_7$i | 1 | — | 1,2,4-Triazolyl-(1) | CO | and the like, as well as salts thereof.

It will be appreciated that the instant specification and examples are set forth by way of illustration and not limitation, and that various modifications and changes may be made without departing from the spirit and scope of the present invention.

What is claimed is:

1. A 1-diaryloxy-1-triazolyl-3,3-dimethyl-butan-2-one or -butan-2-ol of the formula

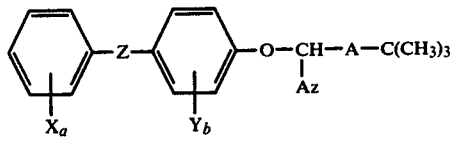

in which
X and Y each independently is halogen, nitro, alkyl with up to 4 carbon atoms, alkoxy with up to 4 carbon atoms, halogenoalkylthio with up to 4 carbon atoms and up to 5 halogen atoms, amino, or alkylamino, dialkylamino or N-alkyl-alkylsulfonamino with up to 4 carbon atoms in each alkyl group,
Z is oxygen, sulfur, methoxy-methylene, ethoxy-methylene, sulfonyl or C=O,
A is C=O or —CH(OH)—,
Az is 1,2,4-triazolyl-(1), 1,2,4-triazolyl-(4) or 1,2,3-triazolyl-(1),
b is 0, 1, 2 or 3, and
a is 1, 2 or 3, and may also be 0 when Z is sulfur, methoxy-methylene, ethoxy-methylene, sulfonyl or C=0,
or a salt thereof.

2. A butanone or butanol according to claim 1, in which X and Y each independently is fluorine, chlorine, bromine, alkyl with up to 4 carbon atoms, alkoxy with up to 4 carbon atoms, halogenoalkylthio with up to 4 carbon atoms and up to 5 halogen atoms, nitro, amino, or alkylamino, dialkylamino or N-alkyl-alkylsulfonylamino with up to 4 carbon atoms in each alkyl group, and a and b each indenpendently is 0, 1 or 2.

3. The compound according to claim 1, wherein such compound is 1-[4'-benzoyl-phenoxy]-1-[1,2,4-triazolyl-(1)]-3,3-dimethylbutan-2-one of the formula

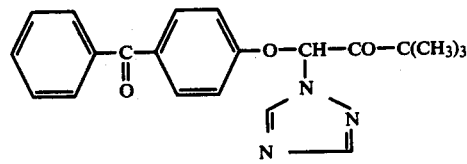

or a salt thereof.

4. The compound according to claim 1, wherein such compound is 1-[4'-(α-methoxybenzyl)-phenoxy]-1-[1,2,4-triazolyl-(1)]-3,3-dimethylbutan-2-ol of the formula

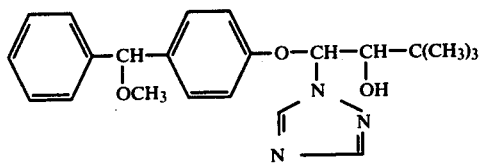

or a salt thereof.

5. The compound according to claim 1, wherein such compound is 1-[4'-phenylsulfonyl-phenoxy]-1-[1,2,4-triazolyl-(1)]-3,3-dimethylbutan-2-ol of the formula

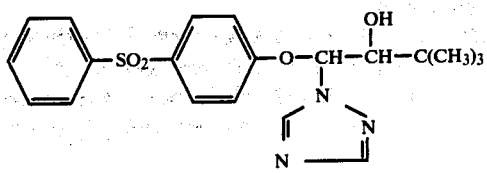

or a salt thereof.

6. A fungicidal composition comprising a diluent and a fungicidally effective amount of a 1-diaryloxy-1-triazolyl-3,3-dimethyl-butan-2-one or -butan-2-ol of the formula

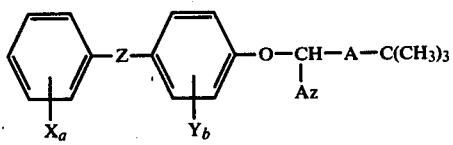

in which
X and Y each independently is halogen, nitro, alkyl with up to 4 carbon atoms, alkoxy with up to 4 carbon atoms, halogenoalkylthio with up to 4 carbon atoms and up to 5 halogen atoms, amino or alkylamino, dialkylamino or N-alkyl-alkylsulfonylamino with up to 4 carbon atoms in each alkyl group,
Z is oxygen, sulfur, methoxy-methylene, ethoxy-methylene, sulfonyl or C=0,
A is C=0 or —CH(OH)—,
Az is 1,2,4-triazolyl-(1), 1,2,4-triazolyl-(4) or 1,2,3-triazolyl-(1),
b is 0, 1, 2 or 3, and
a is 1, 2 or 3 and may also be 0 when Z is sulfur, methoxy-methylene, ethoxy-methylene, sulfonyl or C=0,
or a salt thereof.

7. A method of combating fungi which comprises applying to such fungi or to a fungus habitat a fungicidally effective amount of a 1-diaryloxy-1-triazolyl-3,3-dimethyl-butan-2-one or -butan-2-ol of the formula

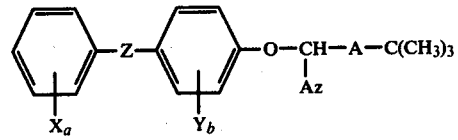

in which
X and Y each independently is halogen, nitro, alkyl with up to 4 carbon atoms, alkoxy with up to 4 carbon atoms, halogenoalkylthio with up to 4 carbon atoms and up to 5 halogen atoms, amino or alkylamino, dialkylamino or N-alkyl-alkylsulfonylamino with up to 4 carbon atoms in each alkyl group,
Z is oxygen, sulfur, methoxy-methylene, ethoxy-methylene, sulfonyl or C=0,
A is C=0 or —(CH(OH)—,
Az is 1,2,4-triazolyl-(1), 1,2,4-triazolyl-(4) or 1,2,3-triazolyl-(1),
b is 0, 1, 2 or 3, and a is 1, 2 or 3 and may also be 0, when Z is sulfur, methoxy-methylene, ethoxy-methylene, sulfonyl or C=0, or a salt thereof.

8. The method according to claim 7, in which said butanone or butanol is 1-[4'-benzoyl-phenoxy]-1-[1,2,4-triazolyl-(1)]-3,3-dimethylbutan-2-one, 1-[4'-(α-methoxybenzyl)-phenoxy]-1-[1,2,4-triazolyl-(1)]-3,3-dimethyl-butan-2-ol or 1-[4'-phenylsulfonyl-phenoxy]-1-[1,2,4-triazolyl-(1)]-3,3-dimethylbutan-2-ol.

9. The method according to claim 7, wherein the compound or a salt thereof with a physiologically tolerated acid is applied to a phytopathogenic fungus of the genus Erysiphe.

10. The method according to claim 7, in which the compound is applied to a plant, seed or soil.

* * * * *